(12) United States Patent
Rutkowski

(10) Patent No.: US 8,124,130 B1
(45) Date of Patent: Feb. 28, 2012

(54) FORMULATIONS AND METHODS FOR RECOVERY FROM DENTAL SURGERY

(75) Inventor: James Louis Rutkowski, Clarion, PA (US)

(73) Assignee: James Louis Rutkowski, Clarion, PA (US)

( * ) Notice: Subject to any disclaimer, the term of this patent is extended or adjusted under 35 U.S.C. 154(b) by 563 days.

(21) Appl. No.: 12/130,913

(22) Filed: May 30, 2008

Related U.S. Application Data

(60) Provisional application No. 60/940,965, filed on May 30, 2007.

(51) Int. Cl.
- *A61K 35/16* (2006.01)
- *A61K 31/573* (2006.01)
- *A61K 38/30* (2006.01)
- *A61K 38/18* (2006.01)
- *A61K 31/4045* (2006.01)

(52) U.S. Cl. ............. 424/532; 424/93.72; 552/574; 514/8.5; 514/8.8; 514/8.9; 514/415

(58) Field of Classification Search .................. None
See application file for complete search history.

(56) References Cited

U.S. PATENT DOCUMENTS

| | | | | |
|---|---|---|---|---|
| 5,736,396 | A * | 4/1998 | Bruder et al. | 435/366 |
| 7,156,880 | B2 * | 1/2007 | Evans et al. | 623/23.51 |
| 7,767,217 | B2 * | 8/2010 | Samson et al. | 424/405 |

OTHER PUBLICATIONS

Jung et al. Platelet-rich plasma and fibrin as delivery systems for recombinant human bone morphogenetic protein-2. Clin Oral Implants Res. Dec. 2005;16(6):676-82.*
Yamaguchi et al. Recombinant human bone morphogenetic protein-2 stimulatesosteoblastic maturation and inhibits myogenic differentiation in vitro. J CellBiol. May 1991;113(3):681-7.*
ChemIDplus Advanced, entry for dexamethasone sodium phosphate. U.S. National Library of Medicine, 8600 Rockville Pike, Bethesda, MD 20894, [retrieved on May 5, 2011]. Retrieved from the Internet<URL: http://chem.sis.nlm.nih.govichemidplus/chemidheavy.jsp>.*
Wermelin et al., Stainless Steel Screws Coated With Bisphosphonates Gave Stronger Fixation and More Surrounding Bone, Bone 42 (2008), available online Dec. 11, 2007, pp. 365-371.
Jakobsen et al., Local Bisphosphonate Treatment Increases Fixation of Hydroxyapatite-Coated Implants Inserted With Bone Compaction, Journal of Orthopaedic Research, Feb. 2009, available online Aug. 27, 2008, pp. 189-194.
Lucarelli et al., Platelet-Derived Growth Factors Enhance Proliferation of Human Stromal Stem Cells, Biomaterials 24 (2003), pp. 3095-3100.
J.P. Frechette, I. Martineau, G. Gagnon, Platelet-rich Plasmas; Growth Factor Content and Roles in Wound Healing, Journal of Dental Research, Jan. 12, 2005, pp. 434-439, J Dent Res 84(50), Sage.
Kasugai, et al., Expression of Bone Matrix Proteins Associated with Mineralized Tissue Formation by Adult Rat Bone Marrow Cells in Vitro: Inductive Effects of Dexamethasone o the Osteoblastic Pheotype, Journal of Cellular Physiology, Jan. 18, 1991, pp. 111-120, vol. 147, Wiley -Liss, Inc.
Miep H. Helfrich, et al., Bone Research Protocols, Mehtods in Molecular Medicine, 2003, pp. 1-18. Humana Press, Inc., Totowa, New Jersey.
Melissa L.M. Khoo, Long-Term Serial Passage and Neuronal Differentiation Capability of Human Bone Marrow Mesenchymal Stem Cells, Stem Cells and Development, Dec. 26, 2007 pp. 883-896, Mary Ann Liebert, Inc.
Xiamjiang Sun, Ph.D, et al., in Vitro Proliferation and Differentiation of Human Mesenchymal Stem Cells Cultured in Autologous Plasma Derived from Bone Marrow, Tissue Engineering, 2008, pp. 391-400, Part A, vol. 14, No. 3, Mary Ann Liebert, Inc.
Isabelle Catelas, PhD, et al., Human Mesenchymal Stem Cell Proliferation and Osteogenic Differentiation in Fibrin Gels in Vitro, Tissue Engineering, 2006, pp. 2385-2396, vol. 12, No. 8, Mary Ann Liebert, Inc.
Neelam Jaiswal, et al., Osteogenic Differentiation of Purified, Culture-Expanded Human Mesenchymal Stem Cells In Vitro, Journal of Cellular Biochemistry, 1997, pp. 295-312, vol. 64, Wiley-Liss, Inc.
Kazuhito Satomura, et al., Melatonin at Pharmacological Doses Enhances Human Osteoblastic Differentiation in Vitro and Promotes Mouse Cortical Bone Formation in Vivo, Journal of Pineal Research, 2007, pp. 231-239, vol. 42, Blackwell Munksgaard.
Nicholas M. Radio, et al., Melatonin Enhances Alkaline Phosphatase Activity in Differentiating Human Adult Mesenchymal Stem Cells Grown in Osteogenic Medium Via MT2 Melatonin Receptors and the MEK/ERK (1/2) Signaling Cascade, Journal of Pineal Research, 2006, pp. 332-342, vol. 40, Blackwell Munksgaard.
Jerome Roth, et al., Melatonin Promotes Osteoblast Differentiation and Bone Formation, The Journal of Biological Chemistry, Jul. 30, 1999, pp. 22041-22047, vol. 274, No. 31.
Barry L. Eppley, M.D., et al., Platelet Quantification and Growth Factor Analysis from Platelet-Rich Plasma: Implications for Wound Healing, 2003, pp. 1502-1508, vol. 114, No. 6.
Philippa Parsons, PhD, et al, Platelet-Rich Concentrate Supports Human Mesenchymal Stem Cell Proliferation, Bone Morphogenetic Proteing-2 Messenger RNA Expression, Alkaline Phosphatase Activity, and Bone Formation In Vitro: A Mode of Action to Enhance Bone Repair, Journal Orthrop Trauma, Oct. 2008, pp. 595-604, vol. 22, No. 9.
Earl G. Freymiller, DMD, MD, et al., Platelet-Rich Plasma: Ready or Not?, Clinical Controversies in Oral and Maxillofacial Surgery: Part One, Journal Oral Maxillofac Surgery, 2004, pp. 484-488, vol. 62.

* cited by examiner

*Primary Examiner* — David Romeo
(74) *Attorney, Agent, or Firm* — Reed Smith LLP

(57) ABSTRACT

Methods and formulations for the improvement of recovery following bone-impacting injury or surgery. The formulations of the present invention preferably include platelet-rich plasma with a pharmaceutical agent. The pharmaceutical agent may be a glucocorticoid hormone or other organic pharmaceutical agent. Particularly preferred pharmaceutical agents include dexamethasone, melatonin, purmorphamine, 17β-estradiol, vitamin $K_2$ (menaquinone-4, MK4), bisphosphonates, derivatives thereof, and combinations thereof. The formulations of the present invention may be directly administered to a surgical or injury site where improved bone growth is desired. The formulations may also be applied to or otherwise incorporated into scaffolding structural components commonly employed in the medical field to promote bone structure and growth. The pharmaceutical agent may be employed in an immediate release form or a sustained release form.

15 Claims, 2 Drawing Sheets

Diff Day 5

Diff Day 15

SEQUENCE LISTING

```
<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
gagtcaacgg atttggtcgt                                           20

<210> SEQ ID NO 2
<211> LENGTH: 20
<212> TYPE: DNA
<213> ORGANISM: Homo sapiens

<400> SEQUENCE: 2
cattgatgac aagcttcccg                                           20

<210> SEQ ID NO 3
<211> LENGTH: 24
<212> TYPE: DNA
<213> ORGANISM: Homo sapiens

<400> SEQUENCE: 3
ctatggagag gacgccacgc ctgg                                      24

<210> SEQ ID NO 4
<211> LENGTH: 23
<212> TYPE: DNA
<213> ORGANISM: Homo sapiens

<400> SEQUENCE: 4
catagccatc gtagccttgt cct                                       23

<210> SEQ ID NO 5
<211> LENGTH: 20
<212> TYPE: DNA
<213> ORGANISM: Homo sapiens
```

```
<400> SEQUENCE: 5
tacctgtatc aatggctggg                                               20

<210> SEQ ID NO 6
<211> LENGTH: 19
<212> TYPE: DNA
<213> ORGANISM: Homo sapiens

<400> SEQUENCE: 6
atgtggtcag ccaactcgt                                                19

<210> SEQ ID NO 7
<211> LENGTH: 19
<212> TYPE: DNA
<213> ORGANISM: Homo sapiens

<400> SEQUENCE: 7
gtcagctgga gcgacgtca                                                19

<210> SEQ ID NO 8
<211> LENGTH: 21
<212> TYPE: DNA
<213> ORGANISM: Homo sapiens

<400> SEQUENCE: 8
ctgaatgccc aaaatacgac g                                             21
```

FORMULATIONS AND METHODS FOR RECOVERY FROM DENTAL SURGERY

This application claims the benefit under 35 U.S.C. §119 (e) of the earlier filing date of U.S. Provisional Application Ser. No. 60/940,965 filed on May 30, 2007.

BACKGROUND OF THE INVENTION

1. Field of the Invention

The present invention relates generally to the field of surgery generally and to dental surgery specifically.

2. Description of the Background

Oral surgeries are performed routinely in the dental field to correct a variety of problems including impacted teeth, infections, periodontally involved teeth, removal of broken or fractured teeth, bone grafts, and/or dental implants. The recovery following dental surgery is often protracted and painful, leading to a great deal of suffering among patients. Following the removal of a tooth, bone formation may take as long as 16 to 24 weeks. Similarly, patients who have suffered a broken bone are commonly confronted with a slow and painful recovery. Accordingly, the medical profession is constantly in search of tools and formulations for the reduction of pain and the improvement of patient recovery time following bone-impacting surgeries or injuries.

Dexamethasone sodium phosphate solution is an FDA-approved, synthetic glucocorticoid steroid hormone. It is commonly employed as an anti-inflammatory agent after surgery. In the laboratory, dexamethasone sodium phosphate solution also been shown to induce osteoblast differentiation in cell culture. Hayami et al. demonstrated that media supplemented with dexamethasone sodium phosphate solution increased osteoblast-specific cell markers in culture. Hayami T, Zhang Q, Kapila Y, Kapila S. "Dexamethsone's enhancement of osteoblast markers in human periodontal ligament cells is associated with inhibition of collagenase expression." *Bone*. (2007) 40(1):93-104.

Platelet-rich-plasma (PRP) is a highly concentrated suspension of platelets with minimal plasma that has been used as a healing aid. To obtain PRP, blood is withdrawn from a patient and centrifuged, resulting in distinct layers in the blood. Through the isolation of one of the layers (buffy coat), a volume of PRP may be obtained. That PRP suspension may be applied to a site of a wound to promote healing. PRP's use has been clinically shown to decrease healing time for patients undergoing surgical procedures (e.g., extractions, bone grafts, implant placement) as well as decrease the incidence of complications resulting from the surgery.

There has been a long-standing need in the oral surgery field for methods and formulations that improve the recovery of patients following bone-impacting injury or surgery. Preferably, such formulations and methods would be able to be implemented routinely and efficiently and would be within the scope of the typical procedures employed by the dental practitioner. The present inventor surprisingly identified formulations in which the beneficial effects of PRP are synergistically improved by the additional of pharmaceutical agents, particularly dexamethasone, Vitamin $K_2$, purmorphamine, melatonin, 17β-estradiol, and bisphosphonates such as alendronate.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

SUMMARY OF THE INVENTION

Figure 1A:
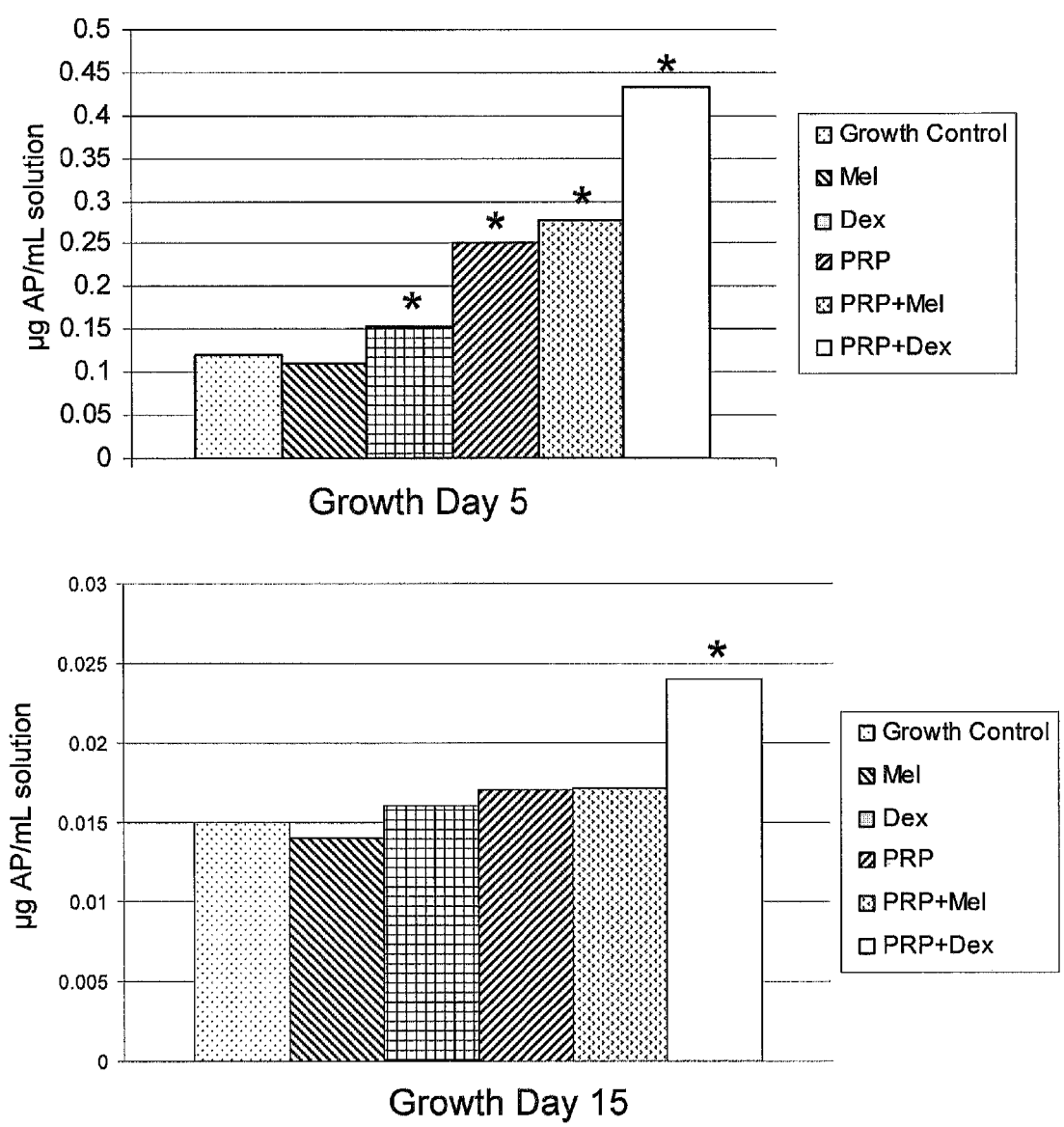
FIG. 1A shows data demonstrating the effect of various pharmaceutical agents on alkaline phosphatase activity in hMSC cultures in growth media.

The present invention is directed to methods and formulations for the improvement of recovery following bone-impacting injury or surgery. In certain preferred embodiments, the formulations of the present invention include platelet-rich plasma and a pharmaceutical agent. The pharmaceutical agent may be selected from the group consisting of dexamethasone, melatonin, purmorphamine, 17β-estradiol, Vitamin $K_2$ (menaquinone-4, MK4), bisphosphonates, derivatives thereof, and combinations thereof. The pharmaceutical agent may be employed in an immediate release form or a sustained release form. The formulations of the present invention may include more than one of the listed pharmaceutical agents, e.g. dexamethasone and melatonin. The formulations of the present invention are preferably administered directly to the surgical site through the use of bone scaffolding structures and may result in dramatic improvement in the recovery time of patients following surgery or injury.

In certain preferred embodiments, a first pharmaceutical agent is co-applied to the surgical site with PRP for several days. Thereafter, a second pharmaceutical agent is applied to the surgical site—either as a sustained release component of the formulation or as a separate administration. In particularly preferred embodiments, the first pharmaceutical agent is dexamethasone and the second pharmaceutical agent is melatonin. These and other formulations of the present invention result in dramatically improved recovery following surgery compared to formulations that include either PRP or the recited pharmaceutical agents alone. In certain presently preferred embodiments, the platelet-rich plasma used in the formulations is obtained from the same patient, on whom the surgery is performed, thus reducing risks and complications from the use of blood products from other individuals.

DETAILED DESCRIPTION OF THE INVENTION

It is to be understood that the figures and descriptions of the present invention have been simplified to illustrate elements that are relevant for a clear understanding of the invention, while eliminating for purposes of clarity, other elements that may be well known. The detailed description will be provided hereinbelow with reference to the attached drawings.

The present invention encompasses formulations and methods for the treatment of patients following bone-impacting surgery or injury. While the present invention is described with regards to dental surgery, the formulations and methods of the present invention are equally applicable to patients recovering from any bone-impacting surgery or injury. The present formulations and methods preferably improve the recovery of patients through generating a synergistic effect between the individual components of the formulation. One benefit of the present invention is an increased rate of bone growth.

In certain preferred embodiments, formulations of the present invention include platelet-rich plasma in combination with a variety of pharmaceutical agents. These formulations may be applied directly to the injury or surgical site as a cellular suspension or as part of a structural plug, scaffold, or other grafting support.

The pharmaceutical compound that is combined with the platelet-rich plasma may be selected from a wide variety of commonly employed reagents. Presently preferred compounds include glucocorticoid hormones (e.g., dexamethasone sodium phosphate). In addition, pharmaceutical agents that possess the characteristic of inducing differentiation of mesenchymal stem cells into osteoblasts may be employed in combination with the PRP and glucocorticoid hormone. Such compounds include, but are not limited to, melatonin, 17β-estradiol, purmorphamine, bisphosphonates (e.g., alendronate, risedronate, ibandronate), and vitamin $K_2$. The present invention may also employ growth factors such as insulin-like growth factor, bone morphogenetic protein, or transforming growth factor-β. The present invention also encompasses formulations that include derivatives or analogs of those recited compounds. Numerous other examples of compounds within those generic groups are well known in the art and could be employed within the context of the present invention as well known to those of skill in the art.

In presently preferred embodiments, the platelet-rich plasma is obtained from the patient on whom the surgery is being performed. That platelet enrichment process may be achieved by standard practices that are currently employed throughout the dental and medical community. In this manner, the formulations of the present invention would avoid any medical complications that might arise from the use of blood products from another individual. The specific volume to be administered to the patient varies widely depending on the type and size of the surgical site. Volumes may range from about 100 microliters to about 1 milliliter per cc of bone grafting material.

Platelet-rich plasma may be obtained in the following manner. Whole blood is drawn from a patient using a 21 gauge 1.5 inch latex-free needle, and 4.5 mL or 9.0 mL vacutainer blood collection tubes containing approximately 0.45-0.9 mL of the anticoagulant trisodium citrate (9:1). The vacutainer tubes are centrifuged for various times at 1150-1350×g using a clinical centrifuge to assess the optimal spin time (typically 6 to 10 minutes) for the recovery of platelets in PRP. After centrifugation, the tubes are removed and placed in a test tube rack on the bench. The red blood cell/plasma interface is allowed to settle for at least 3 minutes. Pre-made labels can be placed on the outside of the tube to reproducibly delineate the PRP layer to be harvested. The PRP layer of the centrifuged blood is then carefully extracted from the suspension.

When employed within the context of the present invention dexamethasone may be used at about 1 to about 1000 nanomoles/milliliter with between about 0.1 and about 2 milliliters being administered to the patient at the surgical site per cc of grafting material.

The concentration of pharmaceutical agent employed in the formulations of the present invention may vary widely depending on the compound itself and the type of surgery or injury from which the patient is recovering. Accordingly, the following concentrations are meant to be illustrative and not limiting. When employed within the context of the present invention melatonin may be used at about 25 to about 500 nanomoles/milliliter with between about 0.1 and about 2 milliliters being administered to the patient at the surgical site per cc of grafting material.

When employed within the context of the present invention purmorphamine may be used at about 0.01 to about 100 micromoles/milliliter with between about 0.1 and about 2 milliliters being administered to the patient at the surgical site per cc of grafting material.

When employed within the context of the present invention 17-β estradiol may be used at about 1 to about 100 nanomoles/milliliter with between about 0.1 and about 2 milliliters being administered to the patient at the surgical site per cc of grafting material.

When employed within the context of the present invention alendronate may be used at about 0.1 nanomoles/milliliter to about 10 micromoles/milliliter with between about 0.1 and about 2 milliliters being administered to the patient at the surgical site per cc of grafting material.

When employed within the context of the present invention Vitamin $K_2$ may be used at about 1 to about 500 micromoles/milliliter with between about 0.1 and about 2 milliliters being administered to the patient at the surgical site per cc of grafting material.

Typically following surgery or injury to bone, a matrix or scaffold is applied to the surgical site to promote bone growth and recovery. The scaffold may take numerous forms including a collagen-containing sheet, plug, or powder. In administering the formulations of the present invention to patients, the PRP and pharmaceutical agents may be mixed with or coated onto the scaffold prior to placement at the surgical site. Other materials may also be used as matrices or scaffolds, such as block, crystal, or powder forms of β-tricalciumphosphate either alone or mixed with a xenograft material with or without collagen; osteoblastic cell sheet with or without a scaffolding matrix; collagen-chitosan-hydroxyapaptite nan-composite scaffolds; poly(3-hydroxybutyrate-co-3-hydroxyhexanoate)-(PHBHHx); poly(3-hydroxybutyrate)-(PHB); poly(3-hydroxybutyrate-co-3-hydroxyvalerate)-(PHBV). Other commonly employed scaffolding materials may also be used within the context of the present invention. The pharmaceutical agent and PRP may be released from the matrix as an immediate one-time bolus or in a delayed or sustained-release manner.

The specific chemical components of the scaffolding structure that support sustained release vary depending on the particular pharmaceutical agent that is employed in the formulation. One of skill in the art is well aware of numerous chemical components that support sustained release, such as silane-based and lactone-based polymers, as well as polylactic acid, polyglycolic acid, polycaprolactone, polyhydroxy butyrate, and copolymers thereof. Furthermore, the pharmaceutical agent or agents may be micro- or nano-encapsulated to provide for their sustained release.

In certain preferred embodiments of the present invention, a formulation that includes dexamethasone, a cellular suspension of PRP, and melatonin is applied to or incorporated into scaffolding material and administered to a patient following oral surgery. In certain particularly preferred embodiments, the PRP suspension and dexamethasone are in an immediate release form. The immediate release form of those components impact many physiological measures, as detailed in the experimental results disclosed below in the examples. Thereby, the formulations of the present invention improve the response of the patient following oral surgery. In those same particularly preferred embodiments, the formulation may include a sustained release component of melatonin which further enhances the osteogenic response of the patient, thereby further improving the rate of healing and recovery from surgery. In certain presently preferred embodiments, the formulation provides for melatonin release that substantially begins after approximately 19 days.

The pharmaceutical agent component of the formulations of the present invention may be initially in powder form. They may then be reconstituted in the cellular suspension at the time of administration for application to the surgical or injury site. Alternatively, the formulations could be formulated in sterile aliquots and stored for extended periods of time prior to administration.

The formulations of the present invention that include a pharmaceutical agent and PRP may also be combined with additional compounds and reagents to improve patient recovery. Those additional reagents may include autogenous bone grafts (e.g., cancellous or cortical), allografts (e.g., irradiated cancellous bone, demineralized freeze-dried bone, mineralized freeze-dried bone), and xenografts. The formulation may also include antibiotics (e.g., neomycin, clindamycin, or polymyxin B).

The present invention may be better understood through the disclosure of the following examples.

Example 1

Human mesenchymal stem cells (hMSCs) were purchased through LONZA BIOSCIENCES. These cells were seeded at a density of approximately 7500 cells/cm$^2$ upon receipt. Since hMSCs spontaneously differentiate into various cell types after 8 to 9 passages, cells passaged 3 to 4 times were used for each of the examples disclosed herein. Supplemented DMEM media was refreshed every third day during culture.

Cultures of hMSCs were passaged in growth medium until a sufficient number of flasks for differentiation studies were obtained. Growth medium was removed and replaced with a variety of experimental solutions as described more fully hereinbelow. For qualitative alkaline phosphatase assays described below, the cells were seeded on collagen coated cover slips (BIOCOAT®) at 2000 cells/cm$^2$. A volume of 3 ml of media was placed into the wells for 5 and 15 days according to the procedures below. For the reverse-transcriptase polymerase chain reaction studies described below, the cells were cultured in their respective media for 5, 10, or 20 days.

Example 2 hMSC cells were grown according to the procedure disclosed in Example 1.

Cells were plated onto cover slips as further described in Example 1. At the time of plating, the growth solution was removed and replaced with: growth medium (as a control), growth medium with 3.5% (v/v) PRP, differentiation medium, growth medium containing dexamethasone ($1\times10^{-7}$ M), growth medium containing melatonin ($3\times10^{-7}$ M), growth medium containing dexamethasone ($1\times10^{-7}$ M) with 3.5% (v/v) PRP, and growth medium containing melatonin ($3\times10^{-7}$ M) with 3.5% (v/v) PRP and incubated for 5 or 15 days.

Similarly, in a parallel set of experiments, cells were also plated using the differentiation media: differentiation medium (as a control), differentiation medium with 3.5% (v/v) PRP, differentiation medium, differentiation medium containing dexamethasone ($1\times10^{-7}$ M), differentiation medium containing melatonin ($3\times10^{-7}$ M), differentiation medium containing dexamethasone ($1\times10^{-7}$ M) with 3.5% (v/v) PRP, and differentiation medium containing melatonin ($3\times10^{-7}$ M) with 3.5% (v/v) PRP and incubated for 5 or 15 days.

At 5 days and 15 days, cultures in each condition were quantitatively assessed for alkaline phosphatase activity (μg of alkaline phosphatase per mL of solution). Quantitative alkaline phosphatase assays (ANASPEC, California) were completed according to manufacturers' instructions. Briefly, the p-nitrophenyl phosphate (pNPP) reaction mixture was diluted 1:100 with dH$_2$O. The AP dilution buffer was prepared by diluting the 10× lysis buffer, with dH$_2$O to have a 1× stock with 1% bovine serum albumin added. The AP standard was diluted 1:25 with dilution buffer. A serial dilution was prepared, from 0.0 to 0.2 ng/uL to create a standard curve. Cells were lysed and 50 μL of lysate or standard, and 50 μL of the pNPP reaction mixture were added. The plate was mixed by gentle shaking for 30 seconds. The plate was incubated at room temperature for 30 minutes and the developing color was measured immediately using a BIO-TEK KINETIC MICROPLATE READER Model EL312E (MTX Lab Systems, Inc, Vienna, Va.) at 405 nm.

Figure 1B:
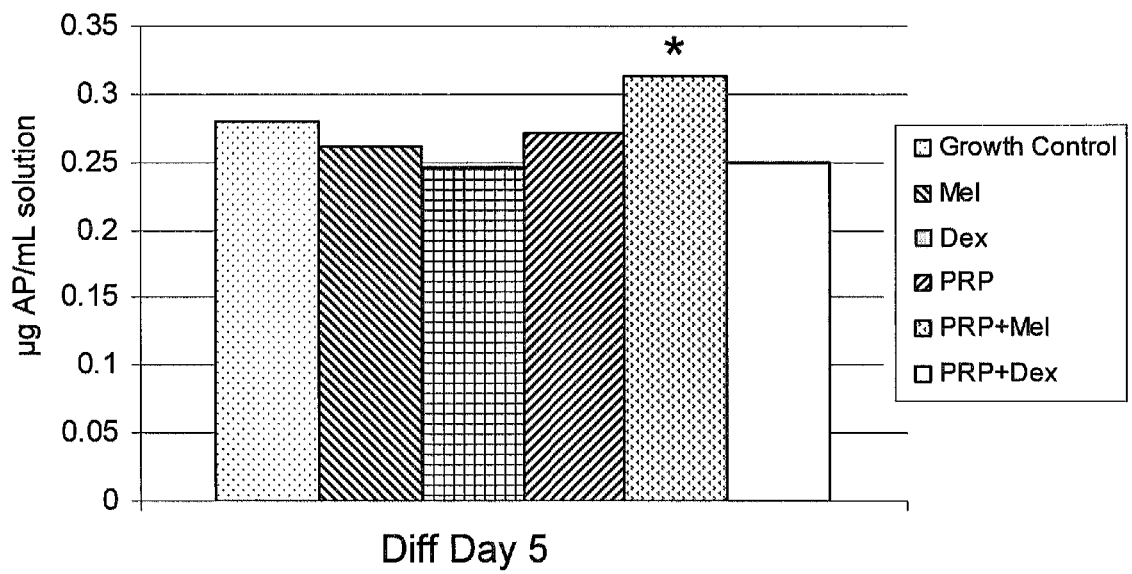
FIG. 1B shows data demonstrating the effect of various pharmaceutical agents on alkaline phosphatase activity in hMSC cultures in differentiation media.
Figure 1B:
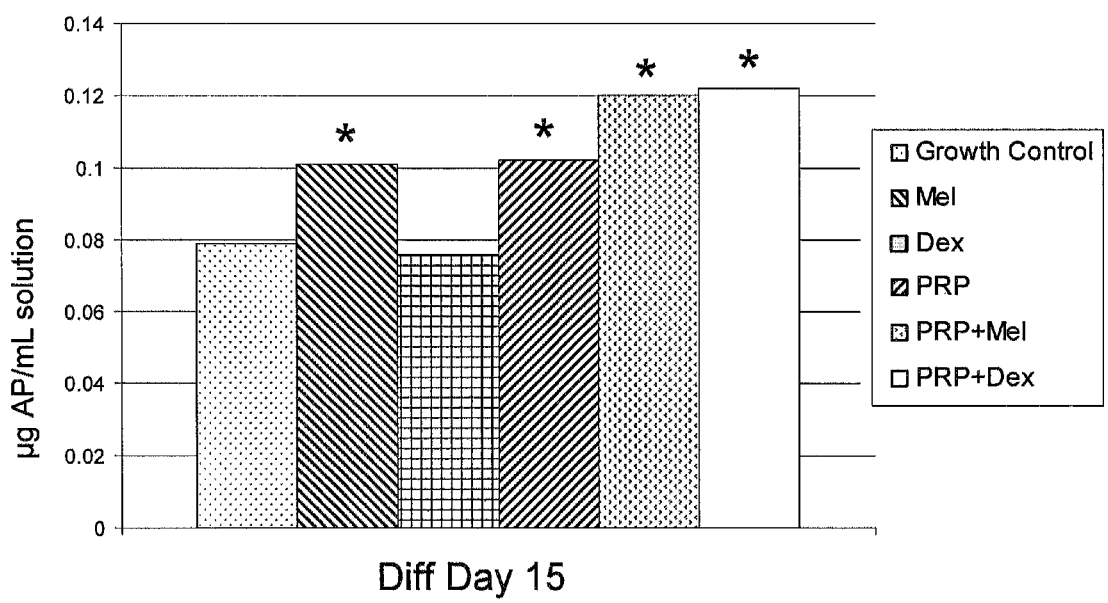

The results of the alkaline phosphatase assays for experiments in growth and differentiation media are shown in FIG. 1. FIG. 1A displays the results for growth media and FIG. 1B shows the results for differentiation media. An asterisk on the chart indicates statistical significance from control cells ($p<0.05$) using the paired t-test (n=9). As may be observed in FIG. 1A, significant effects on alkaline phosphatase activity was observed for PRP-containing growth solutions at Day 5. In particular, synergistic effects of the combination of PRP and dexamethasone were observed. By Day 15, all but the PRP+dexamethasone solutions had returned to baseline levels.

FIG. 1B displays the effects of various pharmacological manipulations on alkaline phosphatase activity of cells grown in differentiation medium. In contrast to the results shown in FIG. 1A, only solutions including PRP and melatonin showed an effect at Day 5. However, at Day 15 solutions including PRP and melatonin showed elevated alkaline phosphatase activity, while solutions containing PRP+melatonin and solutions containing PRP+dexamethasone showed synergistic effects over other solutions.

Example 3

Cells were plated and grown using the general techniques described in Examples 1 and 2. The expression of numerous genes was assessed for cells at Days 5, 10, and 20. Cells were grown in the media as detailed in Tables 1 and 2 below. The expression of the indicated genes was assessed and reported as x-fold increases over the level of normalized gene expression to glyceraldehyde-3-phosphate dehydrogenase (GAPDH) in cells cultured in grown medium (Table 1). An asterisk in the table indicates that the expression of the gene was not detectable.

The genes of interest were selected based upon their appearance in platelets and mesenchymal stem cells differentiating into osteoblasts. Glyceraldehyde-3 phosphate dehydrogenase (GAPDH) is a well characterized housekeeper gene for differentiating hMSCs. The primers used were: forward: 5' GAGTCAACGGATTTGGTCGT (SEQ ID No. 1), reverse: CATTGATGACAAGCTTCCCG (SEQ ID No. 2). The gene for bone sialoprotein (BSP) was chosen because it is expressed during the differentiation of hMSCs, prior to the mineralization phase, but represents a mature functioning osteoblast. The primers were forward: 5' CTATGGAGAG-GACGCCACGCCTGG (SEQ ID No. 3), reverse: CATAGC-CATCGTAGCCTTGTCCT (SEQ ID No. 4). The gene BGLAP (osteocalcin) was chosen because it is definitive marker for functioning osteoblasts at 21 days. The primers were: forward: 5' TACCTGTATCAATGGCTGGG (SEQ ID No. 5), reverse: ATGTGGTCAGCCAACTCGT (SEQ ID No.

6). The gene for glycoprotein-IIβ (GPIIβ or GPIIB) was chosen because it is expressed in developing megakaryocytes and found in platelets. The primers were: forward: GTCAGCTGGAGCGACGTCA (SEQ ID No. 7), reverse: CTGAATGCCCAAAATACGACG (SEQ ID No. 8).

The reaction protocol was completed in a BIO-RAD CHROMO4 Real Time Detection System using the iScript One-Step RT-PCR Kit (BIO-RAD, Hercules, Calif.). Each reaction mixture contained 100 nM of RNA. The 50 μL reaction mixture was placed in the thermal cycler and incubated at 55° C. for 10 minutes, 5 minutes at 95° C. for cDNA synthesis and reverse transcriptase inactivation. The PCR cycling was completed after 45 cycles; 10 seconds at 95° C., 30 seconds at 57° C. A melt curve analysis was completed; 1 minute at 95° C., 1 minute at 55° C., and 10 seconds at 55° C. for 80 cycles, increasing 0.5° C. each cycle. The data was collected and analyzed using the MC OPTICON software. The results are displayed in Tables 1 and 2.

TABLE 1

Values are reported as x-fold increases over the level of normalized gene expression to GAPDH in cells cultured in growth medium (n = 9).
* - below detectable limit.

| Treatment | Gene | Time | | |
|---|---|---|---|---|
| | | Day 5 | Day 10 | Day 20 |
| Differentiation | BSP | 1.35 | 9.75 | 2.18 |
| | GPIIB | 1.09 | 2.05 | 1.46 |
| | Osteocalcin | 1.91 | 2.34 | 1.02 |
| Growth + PRP | BSP | 11.31 | 8.36 | 1.40 |
| | GPIIB | 2.43 | 2.55 | 1.13 |
| | Osteocalcin | 3.80 | 2.45 | 1.715 |
| Differentiation + PRP | BSP | 19.17 | 7.33 | 4.17 |
| | GPIIB | 7.52 | 3.10 | 3.25 |
| | Osteocalcin | 1.97 | 2.93 | * |

TABLE 2

Values are reported as x-fold increase in mRNA expression for each of the pharmacological mediators with and without PRP at the various time points of interest increased compared to untreated growth control (n = 3), * = below detectable limit. Melatonin was present at a concentration of $3 \times 10^{-7}$ molar. Dexamethasone was present at a concentration of $1 \times 10^{-7}$ molar. All experiments reported here were performed in growth media.

| Treatment | Gene | Time | | |
|---|---|---|---|---|
| | | Day 5 | Day 10 | Day 20 |
| Melatonin | Runx2 | 269.75 | 14.39 | 129.83 |
| | GPIIB | * | 968.86 | 2432.97 |
| | Osteocalcin | 260.38 | 1269.3 | 1295.79 |
| Dexamethasone | Runx2 | 138.04 | 4.16 | 15.29 |
| | GPIIB | * | 11.59 | 4993.43 |
| | Osteocalcin | 70.22 | 142.21 | 998.82 |
| Melatonin + PRP | Runx2 | 167.38 | 30.48 | 21.91 |
| | GPIIB | * | 1900.59 | 87.56 |
| | Osteocalcin | 62.36 | 2015.26 | 261.5 |
| Dexamethasone + PRP | Runx2 | 171.42 | 24.24 | 10.86 |
| | GPIIB | * | 4941.77 | 139.91 |
| | Osteocalcin | 42.04 | 7685.47 | 190.91 |

In most cases, PRP treatment appears to induce osteoblastic differentiation of hMSCs, in conjunction with either dexamethasone or melatonin more quickly than is typically observed in standard differentiation medium.

Since many tissues express alkaline phosphatase, another measure was used to verify that the hMSCs were differentiating along the osteoblast/osteocyte lineage. Reverse transcriptase real-time polymerase chain reaction (RT-PCR) was employed to detect changes in gene expression that would indicate osteoblastic differentiation more specifically. The genes that were selected are genes that are expressed at different time points through the development of a mature osteoblast. BSP is expressed between Day 7 and 14. Osteocalcin is expressed late (21 to 30 days) using standard hMSCs and differentiation protocols. To account for possible platelet contribution, expression of GPIIB was evaluated as it is a membrane receptor thought to be exclusively expressed by megakaryocytes and platelets. Typically, the expression of osteocalcin is a definitive marker of osteoblastic differentiation through its role in the production of mineralized matrix.

RT-PCR analysis corroborated the alkaline phosphatase data demonstrating that PRP induced osteoblastic differentiation in hMSCs, as osteoblastic gene expression was much higher and earlier than cells in differentiation medium alone. As expected, BSP is not typically expressed until Days 7 to 14 in standard differentiation medium; it peaks at Day 10 in our system similar to osteocalcin expression. Based on the alkaline phosphatase data, an earlier increase in expression of BSP and osteocalcin was expected and was observed with up regulation of BSP and osteocalcin peaking at Day 5. This earlier increase in expression is seen in cells treated with PRP regardless of the medium used. Osteocalcin expression, however, did not remain elevated at Day 20 in standard differentiation medium even though microscopic examination noted cells that exhibited typical osteoblast morphology and producing mineralized matrix. Even osteoblasts display differences in gene expression, suggesting the existence of osteoblast subpopulations some of which express osteocalcin, while others express BSP.

mRNA expression levels were assessed and the data indicate that co-application of PRP and either dexamethasone or melatonin resulted in higher expression levels than when cells were exposed to PRP alone. For the second PCR run, the gene Runx2 was included instead of BSP. Runx2 is a transcription factor required for all remaining steps of osteoblastic differentiation to occur. Accordingly, it is a specific early marker of osteoblastic differentiation. The highest expression level measured was the dexamethazone+PRP treatment which induced a 7500-fold increase in osteocalcin by Day 10 compared to growth medium alone. This result indicates that these cells are expressing genes typical of end stage osteoblasts/incipient osteocytes that produce mineralized matrix. This result is verified by visual examination of the cells in culture where the accruing mineralized matrix makes it very difficult to document the presence of the underlying cells. Although the osteocalcin expression was highest at Day 10 with dexamethasone+PRP, the melatonin-treated group displayed high levels at Day 5. That result indicates that both compounds affect gene expression at different rates when combined with PRP. Driven by these data, the present invention encompasses combined administration of dexamethasone with PRP at the day of surgery to increase hMSC numbers through proliferation coupled with a delayed release matrix containing melatonin to induce optimal bone formation.

In this study, the gene for glyceraldehyde-3-phosphate dehydrogenase (GAPDH) was used as a "housekeeper" gene, a gene whose expression is typically used in RT-PCR to normalize the expression of other mRNA species on a per cell basis. This study found that PRP treatment not only increased the expression of osteoblast-specific genes but also the housekeeper genes above and beyond what can be accounted for by the number of cells being assayed. PRP treatment therefore globally increased RNA levels. Therefore, treatment with PRP with or without additional supplements affects transcription overall. The increased global transcription of mRNA may allow the hMSCs to metabolically prepare for several rounds of proliferation followed by differentiation and/or migration into wounded areas requiring healing.

Example 4

When dexamethasone and/or melatonin is used in conjunction with PRP and administered to patients using a collagen-type membrane or plug, enhanced clinical healing has been noted in tooth extraction sites following dental surgery. The healing of both bone and soft tissue has increased predictability with a markedly decreased incidence of soft tissue dehiscence. Bone formation is greatly improved both in quality and time necessary for bone formation following treatment using the formulations of the present invention.

When a tooth is removed without placement of a collagen plug impregnated with the pharmacological agents bone formation normally takes 16 to 24 weeks. Under normal conditions a complete bone fill of the socket may not occur even within this time period or even longer. It has been observed on multiple occasions that when the collagen plug or sheet impregnated with either dexamethasone, melatonin, or the combination of both is placed in the extraction site, that bone formation can be noted radiographically and/or with clinical examination upon re-entry to the extraction site in as little as 6-8 weeks. When the bone at the site is prepared for a subsequent implant placement it has been found to be of high quality and most often denser than the adjacent bone that was not treated with the collagen-impregnated plug or sheet. Similar findings have been observed when PRP and the pharmacological agents are applied to either autogenous and/or allograft and/or xenograft bone grafts when osseous reconstruction is performed. Similar results have been observed with or without collagen present. Preliminary observations also indicate a 62% reduction in the likelihood of the development of alveolar osteitis (dry socket) when formulations of the present invention are employed.

Nothing in the above description is meant to limit the present invention to any specific materials, geometry, or orientation of elements. Many pharmacological substitutions are contemplated within the scope of the present invention and will be apparent to those skilled in the art. The embodiments described herein were presented by way of example only and should not be used to limit the scope of the invention.

I claim:

1. A formulation comprising:
   platelet-rich plasma; and
   a pharmaceutical agent, wherein said pharmaceutical agent is dexamethasone.

2. The formulation of claim 1, wherein said formulation is coated onto a bone scaffolding structure.

3. The formulation of claim 1, wherein said formulation is included as a component of a bone scaffolding structure.

4. The formulation of claim 1, wherein said dexamethasone is dexamethasone sodium phosphate.

5. The formulation of claim 4, wherein said dexamethasone sodium phosphate is included at a concentration of about 1 to about 1000 nanomoles/milliliter.

6. The formulation of claim 1, further comprising a growth factor selected from the group consisting of insulin-like growth factor, bone morphogenetic protein, or transforming growth factor-β.

7. The formulation of claim 1, further comprising an organic pharmaceutical agent selected from the group consisting of bisphosphonate, purmorphamine, vitamin $K_2$, and melatonin.

8. The formulation of claim 7, wherein said bisphosphonate is ibandronate, risedronate, or alendronate.

9. The formulation of claim 1, wherein said platelet-rich plasma is present at a volume between about 200 microliters to about 400 microliters.

10. The formulation of claim 2, wherein said scaffolding structure is a collagen sheet or a collagen plug.

11. The formulation of claim 1, further comprising a second pharmaceutical agent.

12. The formulation of claim 11, wherein said dexamethasone is dexamethasone sodium phosphate and said second pharmaceutical agent is melatonin.

13. The formulation of claim 12, wherein said dexamethasone sodium phosphate is in immediate release form and said melatonin is in sustained release form.

14. The formulation of claim 13, wherein said dexamethasone sodium phosphate is at a concentration of about 1 to about 1000 nanomoles/milliliter and said melatonin is at a concentration of about 25 to about 500 nanomoles/milliliter.

15. The formulation of claim 1, wherein said platelet-rich plasma is present as a cellular suspension.

* * * * *